United States Patent
Dai et al.

(10) Patent No.: US 11,344,934 B2
(45) Date of Patent: May 31, 2022

(54) METHOD FOR HARMLESSLY PRETREATING ORGANIC SOLID WASTE BASED ON COMBINATION OF CALCIUM ION AND HYDROTHERMAL TREATMENT

(71) Applicant: TONGJI UNIVERSITY, Shanghai (CN)

(72) Inventors: Xiaohu Dai, Shanghai (CN); Yu Hua, Shanghai (CN)

(73) Assignee: Tongji University, Shanghai (CN)

(*) Notice: Subject to any disclaimer, the term of this patent is extended or adjusted under 35 U.S.C. 154(b) by 0 days.

(21) Appl. No.: 17/528,301

(22) Filed: Dec. 29, 2021

(65) Prior Publication Data

US 2022/0105551 A1    Apr. 7, 2022

(51) Int. Cl.
| | | |
|---|---|---|
| *C02F 1/28* | (2006.01) | |
| *B09B 3/70* | (2022.01) | |
| *B09B 3/40* | (2022.01) | |
| *B09B 3/30* | (2022.01) | |
| *G01N 33/24* | (2006.01) | |
| *B09B 101/65* | (2022.01) | |

(52) U.S. Cl.
CPC .......... *B09B 3/70* (2022.01); *B09B 3/30* (2022.01); *B09B 3/40* (2022.01); *G01N 33/24* (2013.01); *B09B 2101/65* (2022.01)

(58) Field of Classification Search
CPC ...... C02F 1/28; C02F 1/283; C02F 2103/007; C02F 2103/08; C02F 2201/001; A61K 31/105; B01J 20/20; C01B 33/22

USPC .......................................................... 423/331
See application file for complete search history.

(56) References Cited

FOREIGN PATENT DOCUMENTS

| | | |
|---|---|---|
| CA | 2957222 A1 | 2/2016 |
| CN | 102417285 A | 4/2012 |
| CN | 103978013 A | 8/2014 |
| CN | 104845877 A | 8/2015 |
| CN | 107915556 A | 4/2018 |
| CN | 108349968 A | 7/2018 |
| CN | 108721824 A | 11/2018 |
| CN | 108856248 A | 11/2018 |
| CN | 109970303 A | 7/2019 |
| CN | 110573175 A | 12/2019 |
| CN | 111013517 A | 4/2020 |
| CN | 111346897 A | 6/2020 |
| CN | 111620539 A | 9/2020 |
| CN | 211734136 U | 10/2020 |
| JP | 6472098 B2 | 2/2019 |
| KR | 20090036208 A | 4/2009 |

OTHER PUBLICATIONS

Cai C, Yang W, Yang D H, et al. 2020.Hydrothermal treatment of high solid sludge: Harmless performance and bioresource properties[J]. Acta Scientiae Circumstantiae,40(10):3719-3725.

*Primary Examiner* — Edward M Johnson

(57) ABSTRACT

A method for harmlessly pretreating an organic solid waste based on combination of calcium ion and hydrothermal treatment, including: preliminarily screening the organic solid waste followed by addition of calcium ions and hydrothermal treatment to make the organic solid waste harmless.

4 Claims, 1 Drawing Sheet

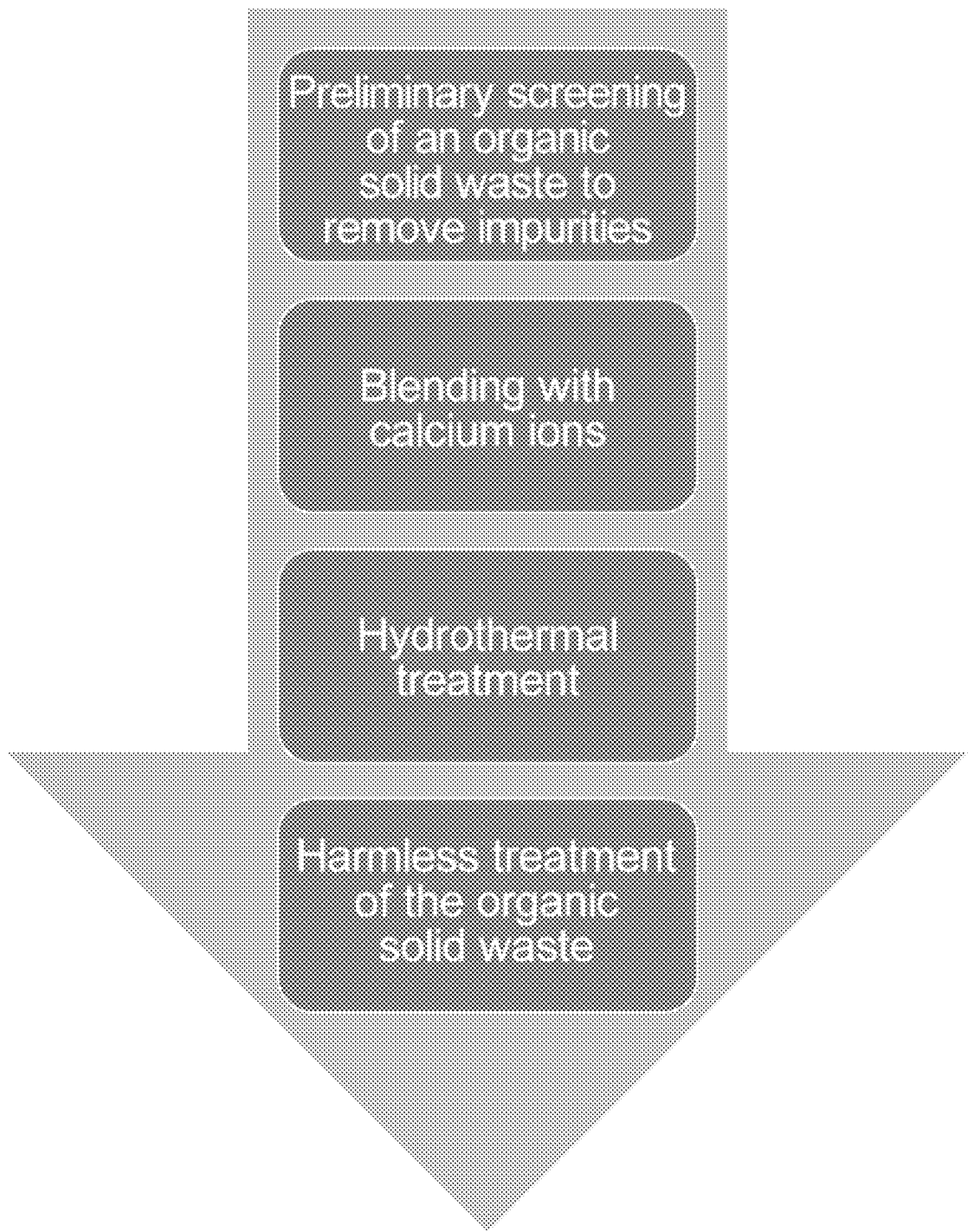

METHOD FOR HARMLESSLY PRETREATING ORGANIC SOLID WASTE BASED ON COMBINATION OF CALCIUM ION AND HYDROTHERMAL TREATMENT

CROSS-REFERENCE TO RELATED APPLICATIONS

This application claims the benefit of priority from Chinese Patent Application No. 202011283766.7, filed on Nov. 17, 2020. The content of the aforementioned application, including any intervening amendments thereto, is incorporated herein by reference.

TECHNICAL FIELD

The present application relates to harmless treatment of organic solid wastes, and more particularly to a method for harmlessly pretreating an organic solid waste based on combination of calcium ion and hydrothermal treatment.

BACKGROUND

In recent years, antibiotics have been extensively used in the fields of clinical medicine, animal husbandry, and aquaculture, and thus a lot of residual antibiotics are continuously discharged into the water. In the biological treatment process of a sewage treatment plant, the antibiotics in sewage is mainly removed by sludge adsorption. It has been demonstrated that more than 70% of the antibiotics adsorbed and enriched by the sludge have not been degraded, which makes the sludge an important antibiotic-carrying medium. Therefore, it is essential to pay attention to the antibiotics in the treatment of sludge. With respect to the animal husbandry, due to the incomplete absorption of antibiotics in animals, high concentrations of antibiotics remain in the feces of livestock and poultry, posing a severe threat to the ecological environment and human health. Moreover, the solid waste produced from the antibiotic production, namely bacterial residue, mainly contains the mycelium of the antibiotic-producing bacteria, unused culture medium, metabolites produced during the fermentation process, degradation products of the culture medium, and a small number of antibiotics. Due to the presence of the residual medium and a small amount of antibiotics and degradation products, the bacterial residue has a potential hazard to the ecological environment, and thus has been widely regarded as a main public hazard of the antibiotic production.

Moreover, the prolonged existence of antibiotics in wastes is an important factor leading to the induction and spread of antibiotic resistance genes (ARGs), and has seriously threatened human health. The common organic solid wastes usually have high microbial biomass, which also provides a potential spreading environment for the horizontal transfer of ARGs. Mobile genetic elements (MEGs) (such as integrons) have been proven to be one of the important ways for human pathogenic bacteria to acquire resistance. Therefore, much attention should be paid to the safety of organic solid waste treatment and disposal, especially the impact on the reduction of antibiotics and ARGs.

SUMMARY

An object of this disclosure is to provide a method for harmlessly pretreating an organic solid waste based on combination of calcium ion and hydrothermal treatment to overcome the defects in the prior art, which can efficiently and conveniently remove toxic and harmful substances (such as fluoroquinolone antibiotic (FQs), antibiotic resistance genes (ARGs), and viruses) from the organic solid waste.

Technical solutions of this application are described as follows.

This application provides a method for harmlessly pretreating an organic solid waste based on combination of calcium ion and hydrothermal treatment, comprising:
introducing a calcium ion-containing reagent to the organic solid waste followed by hydrothermal treatment to make the organic solid waste harmless.

In some embodiments, the organic solid waste is biological sewage sludge, biological wet waste, agricultural straw, manure and dead body of livestock and poultry, industrial bacterial residue, industrial oil sludge, or a combination thereof; and the organic solid waste contains fluoroquinolone antibiotics.

In an embodiment, the method comprises:
(1) screening preliminarily the organic solid waste to remove impurities; and feeding a calcium ion-containing reagent to the organic solid waste followed by adjustment to a water content of 85±5% to form a reaction system;
wherein a dry weight ratio of calcium ions to the organic solid waste is (0.01-0.5):1;
(2) subjecting the reaction system obtained in step (1) to thermal hydrolysis in a closed environment; wherein the thermal hydrolysis is performed at 140-170° C. and 0.8±0.2 MPa for 60±30 min;
(3) after the thermal hydrolysis is completed, cooling the reaction system to 60° C. or less followed by pressure releasing to obtain a treated product; wherein a gas released during the pressure releasing is centralizedly absorbed or collected; and
(4) detecting a content of antibiotics, antibiotic resistance genes and viruses in the treated product obtained in step (3).

The impurities removed by the preliminary screening include large-size suspended solids and some colloids that may block the impeller and pipeline valves and increase the load or wear of the subsequent processing unit, such as plastics, wood, metals and sandstone. By virtue of the introduction of calcium ions, an alkaline environment is created, which can promote the dissolution and degradation of the organic solid waste, facilitating the reduction of organic pollutants and ARGs. The hydrothermal process further enhances the dissolution and degradation of the organic solid waste and promotes the replacement of other heavy metals, facilitating the harmless disposal and the phosphorus recovery.

In some embodiments, the calcium ion-containing agent is calcium oxide or calcium chloride.

In an embodiment, the dry weight ratio of the calcium ions to the organic solid waste is 0.5:1.

In an embodiment, the water content of the reaction system is adjusted to 85%. In an embodiment, the thermal hydrolysis is performed at 170° C. and 0.8 MPa for 90 min.

In some embodiments, the gas released during the pressure releasing is absorbed by using an alkali liquor, or is collected by using a gas film or gas bag.

The beneficial effects of the present disclosure are described as follows.

In the method provided herein, the organic solid waste is screened preliminarily, added with calcium ions and subjected to hydrothermal treatment to realize the high-efficiency and harmless treatment through the synergistic action of the hydrothermal treatment and the calcium ions. After treated by the method provided herein, the content of antibiotics and the absolute abundance of antibiotic resistance genes in the organic solid waste are greatly reduced, and common viruses are all inactivated. The organic solid waste can be further subjected to solid-liquid separation, and an appropriate recycling or disposal strategy or can be selected according to the characteristics of the materials to realize the waste recycling. The method disclosed herein has simple operation, low requirements for equipment, low treatment cost, and excellent treatment effect, and provides a new method and idea for the harmless treatment of organic solid waste.

BRIEF DESCRIPTION OF THE DRAWINGS

To render the technical solutions of the embodiments of this disclosure or the prior art clearer, the drawings used in the description of the embodiments of this disclosure or the prior art will be briefly described below. Obviously, presented in the following drawings are merely some embodiments of the disclosure. Other drawings can be obtained by those skilled in the art based on the drawings provided herein without paying any creative effort.

This FIGURE is a flow chart of a method for harmlessly pretreating an organic solid waste based on combination of calcium ion and hydrothermal treatment according to an embodiment of the present disclosure.

DETAILED DESCRIPTION OF EMBODIMENTS

Various exemplary embodiments of the present disclosure will be described in detail below. The detailed description should not be considered to limit the present disclosure, but should be understood as a more detailed description of certain aspects, characteristics, and embodiments of the present disclosure.

It should be understood that the terms described in the present disclosure are only used to describe specific embodiments and are not intended to limit the present disclosure. In addition, with respect to the numerical range used herein, it should be understood that each intermediate value between the upper limit and the lower limit of the range has also been disclosed specifically. Intermediate values within any stated value or range and each smaller range between any other stated value or intermediate value within the range are also included in the present disclosure. Upper and lower limits of these smaller ranges of can be independently included or excluded from the range.

Unless otherwise specified, all technical and scientific terms used herein have the same meaning as commonly understood by those skilled in the art. Although described herein are only preferred methods and materials, any methods and materials similar or equivalent to those described herein can also be used in the implementation or testing of the present disclosure. All documents mentioned herein are incorporated by reference to disclose and describe methods and/or materials related to the documents.

Without departing from the scope or spirit of the present disclosure, various improvements and changes can be made to the specific embodiments of the present disclosure, which are obvious to those skilled in the art. Other embodiments derived from the description of the present disclosure are obvious to those skilled in the art. The description and embodiments of this application are only exemplary.

As used herein, the terms "comprising", "including", "having", "containing" all have an open meaning, which means including but not limited to.

The organic solid waste used herein is a mixture of sludge, livestock and poultry manure, and industrial bacteria residue, where a ratio of the organic substance content in these components is 1:1:1. Antibiotic standards of ofloxacin, norfloxacin, ciprofloxacin, lomefloxacin are purchased from CNW Technologies Gmbh Company (Germany). Solid-phase extraction cartridges are purchased from Waters Corporation (USA). Chromatographic reagents such as methanol and acetonitrile are purchased from Shanghai Anpu Company and Shanghai Sinopharm Company. The experimental water is deionized water and Millipore water.

The primer sequences used herein are listed as follows:

qnrS:
(SEQ ID NO: 1)
GTGAGTAATCGTATGTACTTTTGCAAACACCTCGACTTAAGTCT;

qnrA:
(SEQ ID NO: 2)
TTCTCACGCCAGGATTTGCCATCCAGATCGGCAAA;

intI1:
(SEQ ID NO: 3)
CGAACGAGTGGCGGAGGGTGTACCCGAGAGCTTGGCACCCA;

human adenovirus:
(SEQ ID NO: 4)
GGACGCCTCGGAGTACCTGAGACRGTGGGGGTTTCTGAACTTGTT;

human polyomavirus:
(SEQ ID NO: 5)
ATGTTTGCCAGTGATGATGAAAAGGAAAGTCTTTAGGGTCTTCTACCT;

human herpes virus:
(SEQ ID NO: 6)
CGGCCGTGTGACACTATCGCTCGTAAAATGGCCCCTCC;

pox virus:
(SEQ ID NO: 7)
TAATACTTCGATTGCTCATCCAGGACTTCTCACAAATGGATTTGAAAAC;

enterovirus:
(SEQ ID NO: 8)
GATTGTCACCATAAGCAGCCCCCTGAATGCGGCTAATC;

human Coronavirus HKU1:
(SEQ ID NO: 9)
GTTGGTTGTATGATGCGTTTGTTCTTCTACAAATAAACTAGCATCAACAT CATCGT;

The detection of antibiotic content is described below. 0.2 g of a sample is added with 20 mL of a basic extraction solution followed by shaking for 5 min to obtain a mixture, where the basic extraction solution is a mixture of triethylamine, methanol, and water in a ratio of 5:25:75. The mixture is subjected to cell disruption at a gradient disruption power, extraction for 5 min, and centrifugation at 5000 r/min for 10 min to collect a supernatant. The above steps are repeated once to obtain another supernatant, and then the supernatants are combined. The combined supernatant is adjusted to pH 3.0 with formic acid, and filtered with a 0.45 μm filter to obtain a filtrate. The filtrate is subjected to dilution, and extraction using a hydrophile-lipophile balance (HLB) solid-phase extraction column. The HLB solid-phase extraction column is activated with 10 mL of methanol and 10 mL of ultrapure water. The liquid sample is passed through the HLB solid-phase extraction column at a flow rate of 5 mL/min, eluted with 5 mL of 5% methanol solution, vacuumed for 10 min under negative pressure, and eluted with 6 ml of 6% ammonia/methanol eluent to obtain an elution solution. The elution solution is dried with nitrogen in a water bath at 35° C., diluted to a volume of 1 mL using the initial mobile phase, filtered with the 0.45 μm pinhole-filtration membrane, and stored in chromatographic vials to be tested. The test is performed on an Agilent technologies 1260 high-performance liquid chromatography (HPLC) equipped with a fluorescence detector, where the mobile phase consists of phosphoric acid-triethylamine solution (A) and methanol (B) in a ratio of 80%:20%; the pH of the phosphoric acid-triethylamine solution is 3.0; an Agilent XDB-c18 column (150 mm*4.6 mm, 5.0 μm) is employed; the injection volume is 20 μm; the flow rate is 1 mL/min; the column temperature is 30° C.; and the analysis time for each sample is 18 min; the scanning wavelength is programmed as follows: 0-9.5 min: the excitation wavelength and emission wavelength are respectively 295 nm and 500 nm; 9.5-14 min: the excitation wavelength and emission wavelength are respectively 278 nm and 445 nm; and 14-18 min: the excitation wavelength and emission wavelength are respectively 285 nm and 470 nm.

The detection of antibiotic resistance genes is performed as the following steps. 10 g of each homogeneous sample (original sample or hydrothermal product) is freeze-dried in a −80° C. ultra-low temperature refrigerator for 48 h. 0.25 g of the freeze-dried sample is subjected to extraction using a Fast DNA∘R Spin kit (MP Bimedicals). The DNA concentration is monitored using the QuantiFluor ∘R dsDNA system (Promega). The ViiATM 7 real-time PCR system is configured to perform quantitative PCR reaction. FQs resistance genes (qnrS and qnrA), an integrase gene intL1 and a 16S rRNA-encoding gene are selected for detection.

The extraction and detection of viruses are performed as follows. 10 g of the organic solid waste is mixed with 50 mL of an eluent (10% beef extract, pH=7.2), stirred at 5000 r/min at room temperature for 30 min, and centrifuged at 4° C. and 10000 g for 30 min to collect a supernatant liquid. The supernatant is adjusted to pH 7.2. The supernatant liquid is filtered by a 0.22 μm filter membrane to remove residual bacterial fragments. The filtration fluid is added with 8% polyethylene glycol followed by mixing, standing at 4° C. for 12 h, centrifugation at 4° C. and 12000 g for 30 min. After that, the precipitation is collected to perform the extraction and detection of DNA and RNA directly.

EXAMPLE 1

Provided herein was a method for harmlessly pretreating an organic solid waste, which was specifically described as follows (as shown in the FIGURE).

(S1) Blending with Calcium Ions

An organic solid waste was screened preliminarily to remove impurities. 70 g of the screened organic solid waste was added with 1 g of calcium oxide to form a reaction system. A water content of the reaction system was adjusted to 80%.

(S2) Harmless Disinfection by Hydrothermal Treatment

The reaction system obtained in step (1) was subjected to thermal hydrolysis in a closed container, where the thermal hydrolysis was performed at 140° C. and 0.6 MPa for 30 min.

(S3) Cooling and Pressure Releasing

After the thermal hydrolysis was completed, the reaction system was cooled to 60° C. or less, followed by opening a pressure-releasing valve to perform pressure releasing, where a gas released during the pressure releasing was centralizedly absorbed by using an alkali liquor, or was collected by using a gas film or gas bag.

(S4) Detection of a Content of Antibiotics

Antibiotics, resistance genes and viruses in the treated product obtained in step (3) were detected according to the above-mentioned detection methods.

EXAMPLE 2

Provided herein was a method for harmlessly pretreating an organic solid waste, which was specifically described as follows.

(S1) Blending with Calcium Ions

An organic solid waste was screened preliminarily to remove impurities. 70 g of the screened organic solid waste was added with 97 g of calcium chloride to form a reaction system. A water content of the reaction system was adjusted to 85%.

(S2) Harmless Disinfection by Hydrothermal Treatment

The reaction system obtained in step (1) was subjected to thermal hydrolysis in a closed container, where the thermal hydrolysis was performed at 170° C. and 0.8 MPa for 90 min.

(S3) Cooling and Pressure Releasing

After the thermal hydrolysis was completed, the reaction system was cooled to 60° C. or less, followed by opening a pressure-releasing valve to perform pressure releasing, where a gas released during the pressure releasing was centralizedly absorbed or collected.

(S4) Detection of a Content of Antibiotics

Antibiotics, resistance genes and viruses in the treated product obtained in step (3) were detected according to the above-mentioned detection methods.

EXAMPLE 3

Provided herein was a method for harmlessly pretreating an organic solid waste, which was specifically described as follows.

(S1) Blending with Calcium Ions

An organic solid waste was screened preliminarily to remove impurities. 70 g of the screened organic solid waste was added with 90 g of calcium oxide to form a reaction system. A water content of the reaction system was adjusted to 90%.

(S2) Harmless Disinfection by Hydrothermal Treatment

The reaction system obtained in step (1) was subjected to thermal hydrolysis in a closed container, where the thermal hydrolysis was performed at 160° C. and 1.0 MPa for 60 min.

(S3) Cooling and Pressure Releasing

After the thermal hydrolysis was completed, the reaction system was cooled to 60° C. or less, followed by opening a pressure-releasing valve to perform pressure releasing, where a gas released during the pressure releasing was centralizedly absorbed or collected.

(S4) Detection of a Content of Antibiotics Antibiotics, resistance genes and viruses in the treated product obtained in step (3) were detected according to the above-mentioned detection methods.

EXPERIMENTAL RESULTS

The experimental results were described below.

TABLE 1

Effects of combination of calcium ion and hydrothermal treatment on degradation of antibiotics in organic solid wastes

| | Antibiotic content (mg/kg) | | | |
|---|---|---|---|---|
| Samples | Lomefloxacin | Ciprofloxacin | Norfloxacin | Ofloxacin |
| Original organic solid waste | 0.32 | 0.61 | 1.56 | 8.04 |
| Example 1 | 0.24 | 0.45 | 1.48 | 6.43 |
| Example 2 | 0 | 0 | 1.31 | 3.61 |
| Example 3 | 0.12 | 0.13 | 1.33 | 4.34 |

It can be seen from Table 1 that the residual amount of antibiotics in the organic solid waste had been decreased significantly after combination of calcium ion and hydrothermal treatment, proving that combination of calcium ion and hydrothermal treatment could accelerate the degradation rate of antibiotics in the organic solid waste.

TABLE 2

Effects of combination of calcium ion and hydrothermal treatment on absolute abundance of resistance genes of quinolone antibiotics in organic solid wastes

| | Absolute abundance of resistance genes (copies/g) | | | |
|---|---|---|---|---|
| Samples | qnrS | qnrA | Intl1 | 16S rDNA gene |
| Original organic solid waste | $1.09 \times 10^{11}$ | $1.01 \times 10^{10}$ | $0.98 \times 10^{8}$ | $10^{12}$ |
| Example 1 | $1.03 \times 10^{7}$ | $1.07 \times 10^{7}$ | $2.11 \times 10^{5}$ | $10^{9}$ |
| Example 2 | $1.03 \times 10^{5}$ | — | — | $10^{7}$ |
| Example 3 | $8.92 \times 10^{5}$ | $2.08 \times 10^{5}$ | $3.81 \times 10^{3}$ | $10^{8}$ |

It can be seen from Table 2 that the absolute abundance of resistance genes of quinolone antibiotics in organic solid wastes had been greatly reduced after combination of calcium ion and hydrothermal treatment, proving that the combination of calcium ion and hydrothermal treatment could significantly reduce the resistance genes of quinolone antibiotics of organic solid wastes.

TABLE 3

Effect of combination of calcium ion and hydrothermal treatment on absolute abundance of resistance genes of quinolone antibiotics in organic solid waste

| | DNA virus | | | | RNA virus | |
|---|---|---|---|---|---|---|
| Samples | Adenovirus huminis | Herpesvirus | Polyomavirus | Poxvirus | Enterovirus | Coronavirus |
| Original organic solid waste | + | + | + | + | + | + |
| Example 1 | − | − | − | − | − | − |
| Example 2 | − | − | − | − | − | − |
| Example 3 | − | − | − | − | − | − |

Notes:
"+" represents positive;
"−" represents negative.

Common viruses in organic solid wastes, including four kinds of DNA viruses (human adenovirus, herpes virus, polyoma virus, and pox virus) and 2 kinds of RNA viruses (enterovirus and human coronavirus) were detected herein to evaluate the effects of combination of calcium ion and hydrothermal treatment on virus killing.

The experimental results showed that after treated through the combination of calcium ion and hydrothermal treatment, the organic solid waste was tested negative for the 6 kinds of viruses, indicating that the method disclosed herein could effectively eliminate viruses in the organic solid waste.

Described above are merely preferred embodiments of this application, which are not intended to limit the application. It should be understood that modifications and replacements made by those skilled in the art without departing from the spirit of the application should fall within the scope of the application defined by the appended claims.

What is claimed is:

1. A method for harmlessly pretreating an organic solid waste, comprising;
   (1) screening preliminarily the organic solid waste to remove impurities; and
   feeding a calcium ion-containing reagent to the organic solid waste followed by adjustment to a water content of 85±5% to form a reaction system;
   (2) subjecting the reaction system obtained in step (1) to thermal hydrolysis in a closed environment; wherein the thermal hydrolysis is performed at 140-170° C. and 0.8±0.2 MPa for 60±30 min;
   (3) after the thermal hydrolysis is completed, cooling the reaction system to 60° C. or less, followed by pressure releasing to obtain a treated product; wherein a gas released during the pressure releasing is centralizedly absorbed or collected; and
   (4) detecting a content of antibiotics, antibiotic resistance genes and viruses in the treated product obtained in step (3);
   wherein the calcium ion-containing reagent is calcium chloride; a dry weight ratio of the calcium ions to the organic solid waste is 0.5:1; the organic solid waste is biological sewage sludge, biological wet waste, agricultural straw, manure and dead body of livestock and poultry, industrial bacterial residue, industrial oil sludge, or a combination thereof; and the organic solid waste contains fluoroquinolone antibiotics.

2. The method of claim 1, wherein the water content of the reaction system is adjusted to 85%.

3. The method of claim 1, wherein the thermal hydrolysis is performed at 170° C. and 0.8 MPa for 90 min.

4. The method of claim 1, wherein the gas for pressure releasing is absorbed by using an alkali liquor, or is collected by using a gas film or gas bag.

\* \* \* \* \*